United States Patent
Barger et al.

(10) Patent No.: US 6,534,692 B1
(45) Date of Patent: *Mar. 18, 2003

(54) METHANOL TO OLEFIN PROCESS WITH INCREASED SELECTIVITY TO ETHYLENE AND PROPYLENE

(75) Inventors: Paul T. Barger, Arlington Heights, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 37 days.

This patent is subject to a terminal disclaimer.

(21) Appl. No.: 09/816,509

(22) Filed: Mar. 23, 2001

Related U.S. Application Data

(63) Continuation-in-part of application No. 09/305,960, filed on May 6, 1999, now Pat. No. 6,207,872, which is a continuation-in-part of application No. 08/987,085, filed on Dec. 9, 1997, now Pat. No. 5,912,393.

(51) Int. Cl.⁷ ................................................. C07C 1/00

(52) U.S. Cl. ...................................... 585/640; 585/639

(58) Field of Search ................................ 585/639, 640, 585/642

(56) References Cited

U.S. PATENT DOCUMENTS

| | | | |
|---|---|---|---|
| 4,238,631 A | 12/1980 | Daviduk et al. | 585/469 |
| 4,328,384 A | 5/1982 | Daviduk et al. | 585/469 |
| 4,423,274 A | 12/1983 | Daviduk et al. | 585/640 |
| 4,499,327 A | 2/1985 | Kaiser | 585/640 |
| 4,752,651 A | 6/1988 | Kaiser | 585/640 |
| 5,126,308 A | 6/1992 | Barger et al. | 502/214 |
| 5,912,393 A | 6/1999 | Barger et al. | 585/640 |
| 6,207,872 B1 * | 3/2002 | Barger et al. | 585/640 |

* cited by examiner

Primary Examiner—Tom Dunn
Assistant Examiner—Christina Ildebrando
(74) Attorney, Agent, or Firm—John G. Tolomei; Frank S. Molinaro

(57) ABSTRACT

A process for converting methanol to light olefins is disclosed and claimed. The catalyst is a metalloaluminophosphate molecular sieve having the empirical formula $(E_xAl_yP_z)O_2$ where EL is a metal such as silicon or magnesium and "x", "y" and "z" are the mole fractions of EL, Al and P respectively and specifically where "x" has a value of about 0.02 to about 0.08. A preferred molecular sieve is one which has predominantly a plate crystal morphology in which the average smallest crystal dimension is at least 0.1 microns and has an aspect ratio of no greater than 5. The process provides greater selectivity to ethylene and propylene versus $C_{4+}$ byproducts.

23 Claims, No Drawings

METHANOL TO OLEFIN PROCESS WITH INCREASED SELECTIVITY TO ETHYLENE AND PROPYLENE

CROSS-REFERENCE TO RELATED APPLICATION

This application is a continuation-in-part of U.S. application Ser. No. 09/305,960, filed May 6, 1999 and issued as U.S. Pat. No. 6,207,872 B1 which in turn is a continuation-in-part of U.S. application Ser. No. 08/987,085 filed Dec. 9, 1997, now U.S. Pat. No. 5,912,393 B1 all of which are incorporated by reference.

FIELD OF THE INVENTION

This invention relates to a process for converting methanol to light olefins with increased selectivity to ethylene and propylene. The process comprises contacting the methanol with a catalyst comprising a metallo aluminophosphate molecular sieve having an empirical formula of $(EL_xAl_yP_z)O_2$ where EL includes silicon and characterized in that "x" has a value from about 0.02 to about 0.08. A preferred catalyst is one where the molecular sieve has predominantly a plate crystal morphology such that the average smallest crystal dimension is at least 0.1 micron and has an aspect ratio of less than or equal to 5.

BACKGROUND OF THE INVENTION

The limited supply and increasing cost of crude oil has prompted the search for alternative processes for producing hydrocarbon products. One such process is the conversion of methanol to hydrocarbons and especially light olefins (by light olefins is meant $C_2$ to $C_4$ olefins). The interest in the methanol to olefin (MTO) process is based on the fact that methanol can be obtained from coal or natural gas by the production of synthesis gas which is then processed to produce methanol.

Processes for converting methanol to light olefins are well known in the art. Initially aluminosilicates or zeolites were used as the catalysts necessary to carry out the conversion. For example, see U.S. Pat. No. 4,238,631 B1; U.S. Pat. No. 4,328,384 B1, U.S. Pat. No. 4,423,274 B1. These patents further disclose the deposition of coke onto the zeolites in order to increase selectivity to light olefins and minimize the formation of $C_{5+}$ byproducts. The effect of the coke is to reduce the pore diameter of the zeolite.

The prior art also discloses that silico aluminophosphates (SAPOs) can be used to catalyze the methanol to olefin process. Thus, U.S. Pat. No. 4,499,327 B1 discloses that many of the SAPO family of molecular sieves can be used to convert methanol to olefins. The '327 patent also discloses that preferred SAPOs are those that have pores large enough to adsorb xenon (kinetic diameter of 4.0 Å) but small enough to exclude isobutane (kinetic diameter of 5.0 Å). A particularly preferred SAPO is SAPO-34.

U.S. Pat. No. 4,752,651 B1 discloses the use of non-zeolitic molecular sieves (NZMS) including ELAPOs and MeAPO molecular sieves to catalyze the methanol to olefin reaction.

The effect of the particle size of the molecular sieve on activity has also been documented in U.S. Pat. No. 5,126,308 B1. In the '308 patent it is disclosed that molecular sieves in which 50% of the molecular sieve particles have a particle size less than 1.0 µm and no more than 10% of the particles have a particle size greater than 2.0 µm have increased activity and/or durability. The '308 patent also discloses that restricting the silicon content to about 0.005 to about 0.05 mole fraction also improves catalyst life by reducing coke formation.

In contrast to this art, applicants have found that a methanol to olefin process using molecular sieves having the empirical formula $(EL_xAl_yP_z)O_2$ (hereinafter ELAPO) where EL is a metal selected from the group consisting of silicon, magnesium, zinc, iron, cobalt, nickel, manganese, chromium and mixtures thereof and "x", "y" and "z" are the mole fractions of EL, Al and P respectively and specifically where "x" has a value from about 0.02 to about 0.08 provides an increased selectivity to ethylene and propylene with a reduction in undesirable $C_{4s}$ and $C_{5+}$. A preferred catalyst is one which additionally has a predominantly plate crystal morphology wherein the average smallest crystal dimension is at least 0.1 micron and has an aspect ratio of less than or equal to 5

SUMMARY OF THE INVENTION

As stated, this invention relates to a process for converting methanol to light olefins using a catalyst comprising an ELAPO molecular sieve. Accordingly, one embodiment of the invention is a process for converting methanol to light olefins comprising contacting the methanol with a catalyst at conversion conditions to provide the olefins, the catalyst comprising a crystalline metallo aluminophosphate molecular sieve having a chemical composition on an anhydrous basis expressed by an empirical formula of:

$$(EL_xAl_yP_z)O_2$$

where EL is a metal selected from the group consisting of silicon, magnesium, zinc, iron, cobalt, nickel, manganese, chromium and mixtures thereof, "x" is the mole fraction of EL and has a value of about 0.02 to about 0.08, "y" is the mole fraction of Al and has a value of at least 0.01, "z" is the mole fraction of P and has a value of at least 0.01 and x+y+z=1.

In another embodiment, the molecular sieve is characterized in that it has a crystal morphology wherein the average smallest crystal is at least 0.1 micron and has an aspect ratio no greater than 5.

These and other objects and embodiments of the invention will become more apparent after the detailed description of the invention.

DETAILED DESCRIPTION OF THE INTENTION

An essential feature of the process of the instant invention is an ELAPO molecular sieve. ELAPOs are molecular sieves which have a three-dimensional microporous framework structure of $AlO_2$, $PO_2$ and $ELO_2$ tetrahedral units. Generally the ELAPOs have the empirical formula:

$$(EL_xAl_yP_z)O_2$$

where EL is a metal selected from the group consisting of silicon, magnesium, zinc, iron, cobalt, nickel, manganese, chromium and mixtures thereof, "x" is the mole fraction of EL and has a value of at least 0.005, "y" is the mole fraction of Al and has a value of at least 0.01, "z" is the mole fraction of P and has a value of at least 0.01 and x+y+z=1. When EL is a mixture of metals, "x" represents the total amount of the metal mixture present. Preferred metals (EL) are silicon, magnesium and cobalt with silicon being especially preferred. As will be shown in the examples, when "x" has a value of about 0.02 to about 0.08 a greater selectivity to ethylene and propylene with a diminished selectivity to $C_{4+}$ components is observed.

The preparation of various ELAPOs are well known in the art and may be found in U.S. Pat. No. 4,554,143 B1 (FeAPO); U.S. Pat. No. 4,440,871 B1 (SAPO); U.S. Pat. No. 4,853,197 B1 (MAPO, MnAPO, ZnAPO, COAPO); U.S. Pat. No. 4,793,984 B1 (CAPO), U.S. Pat. No. 4,752,651 B1 and U.S. Pat. No. 4,310,440 B1, all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

The reaction mixture is placed in a sealed pressure vessel, optionally lined with an inert plastic material such as polytetrafluoroethylene and heated preferably under autogenous pressure at a temperature between about 50° C. and 250° C. and preferably between about 100° C. and 200° C. for a time sufficient to produce crystals of the ELAPO molecular sieve. Typically the time varies from about 1 hour to about 120 hours and preferably from about 24 hours to about 48 hours. The desired product is recovered by any convenient method such as centrifugation or filtration.

The ELAPO molecular sieves of this invention have predominantly a plate crystal morphology. By predominantly is meant greater than 50% of the crystals. Preferably at least 70% of the crystals have a plate morphology and most preferably at least 90% of the crystals have a plate morphology. Especially good selectivity ($C_2^=$ versus $C_3^=$) is obtained when at least 95% of the crystals have a plate morphology. By plate morphology is meant that the crystals have the appearance of rectangular slabs. More importantly, the aspect ratio is less than or equal to 5. The aspect ratio is defined as the ratio of the largest crystalline dimension divided by the smallest crystalline dimension. A preferred morphology which is encompassed within the definition of plate is cubic morphology. By cubic is meant not only crystals in which all the dimensions are the same, but also those in which the aspect ratio is less than or equal to 2. It is also necessary that the average smallest crystal dimension be at least 0.1 microns and preferably at least 0.2 microns.

As is shown in the examples, the morphology of the crystals and the average smallest crystal dimension is determined by examining the ELAPO molecular sieve using Scanning Electron Microscopy (SEM) and measuring the crystals in order to obtain an average value for the smallest dimension.

Without wishing to be bound by any one particular theory, it appears that a minimum thickness is required so that the diffusion path for the desorption of ethylene and propylene is sufficiently long to allow differentiation of the two molecules. Since ethylene is a more valuable product, by controlling the crystal dimensions one can maximize the formation of ethylene. As will be shown in the examples, when the smallest dimension is less than 0.1, the ratio of ethylene to propylene ($C_2^=/C_3^=$) is about 1.2, whereas when the smallest dimension is greater than 0.1 microns, the ratio of $C_2^=/C_3^=$ is about 1.4. This provides a greater production of ethylene.

The ELAPOs which are synthesized using the process described above will usually contain some of the organic templating agent in its pores. In order for the ELAPOs to be active catalysts, the templating agent in the pores must be removed by heating the ELAPO powder in an oxygen containing atmosphere at a temperature of about 200° to about 700° C. until the template is removed, usually a few hours.

As stated above unexpected selectivity is obtained when the metal (EL) content varies from about 0.02 to about 0.08 mole fraction, preferably from about 0.02 to about 0.07 and more preferably from about 0.03 to about 0.068. If EL is more than one metal then the total concentration of all the metals is between about 0.02 and 0.08 mole fraction. An especially preferred embodiment is one in which EL is silicon (usually referred to as SAPO). The SAPOs which can be used in the instant invention are any of those described in U.S. Pat. No. 4,440,871 B1. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å.

The ELAPO molecular sieve of this invention may be used alone or they may be mixed with a binder and formed into shapes such as extrudates, pills, spheres, etc. Any inorganic oxide well known in the art may be used as a binder. Examples of the binders which can be used include alumina, silica, aluminum-phosphate, silica-alumina, etc. When a binder is used, the amount of ELAPO which is contained in the final product ranges from 10 to 90 weight percent and preferably from 30 to 70 weight percent.

The conversion of methanol to light olefins is effected by contacting the methanol with the ELAPO catalyst at conversion conditions, thereby forming the desired light olefins. The methanol can be in the liquid or vapor phase with the vapor phase being preferred. Contacting the methanol with the ELAPO catalyst can be done in a continuous mode or a batch mode with a continuous mode being preferred. The amount of time that the methanol is in contact with the ELAPO catalyst must be sufficient to convert the methanol to the desired light olefin products. When the process is carried out in a batch process, the contact time varies from about 0.001 hr. to about 1 hr. and preferably from about 0.01 hr. to about 1.0 hr. The longer contact times are used at lower temperatures while shorter times are used at higher temperatures. Further, when the process is carried out in a continuous mode, the Weight Hourly Space Velocity (WHSV) based on methanol can vary from about 1 $hr^{-1}$ to about 1000 $hr^{-1}$ and preferably from about 1 $hr^{-1}$ to about 100 $hr^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e.g., methane, aromatic hydrocarbons, e.g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art.

Thus, a single reaction zone or a number of zones arranged in series or parallel may be used. In such reaction zones the methanol feedstock is flowed through a bed containing the ELAPO catalyst. When multiple reaction zones are used, one or more ELAPO catalyst may be used in series to produce the desired product mixture. Instead of a fixed bed, a dynamic bed system, e.g., fluidized or moving, may be used. Such a dynamic system would facilitate any regeneration of the ELAPO catalyst that may be required. If regeneration is required, the ELAPO catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims.

EXAMPLE 1

A series of molecular sieves (SAPOs) were prepared by the following procedure. In a container orthophosphoric acid (85%) was combined with water. To this there was added a silica sol and a 35 wt. % aqueous solution of tetraethylammonium hydroxide (TEAOH). Finally, alumina in the form of pseudo-boehmite along with water and SAPO-34 seed material were added and blended in. The resulting mixtures had compositions in molar oxide ratios as set forth in Table 1 below.

TABLE 1

Reaction Mixture Compositions For SAPOs

| Sample I.D. | Reaction Time | TEAOH | $SiO_2$ | $Al_2O_3$ | $P_2O_5$ | $H_2O$ |
|---|---|---|---|---|---|---|
| A | 48 | 1.0 | 0.10 | 1.0 | 1.0 | 35 |
| B | 48 | 1.0 | 0.10 | 1.0 | 1.0 | 35 |
| C | 48 | 1.0 | 0.10 | 1.0 | 1.0 | 45 |
| D | 24 | 1.0 | 0.10 | 1.0 | 1.0 | 45 |
| E | 36 | 1.0 | 0.15 | 1.0 | 1.0 | 40 |
| F | 48 | 1.0 | 0.20 | 1.0 | 1.0 | 45 |

The mixture was now placed in a steel pressure reactor equipped with a turbine stirrer. The mixture was now stirred and heated to 100° C. over a 6 hour period, held at 100° C. for 6 hours, then heated to 175° C. over a period of 3 hours and held there for the reaction time of 24, 36 or 48 hours. Finally, the reaction mixture was cooled to ambient temperature and the solid product recovered by centrifugation and washed with water. All the products were analyzed and found to be SAPO-34 molecular sieves.

EXAMPLE 2

The catalysts prepared in Example 1 were evaluated for the conversion of methanol to light olefins in a fixed bed pilot plant. A 4 gram sample in the form of 20–40 mesh agglomerates was used for the testing. Before testing, each sample was calcined in air in a muffle oven at 650° C. for 2 hours and then pretreated in situ by heating to 400° C. for 1 hour under nitrogen. The pretreated sample was now contacted with a feed consisting of methanol and $H_2O$ in a 1/0.44 molar ratio at 435° C., 5 psig and 2.5 $hr^{-1}$ MeOH WHSV. The composition of the effluent was measured by an on-line GC after 30 minutes on stream to determine initial conversion and selectivities. Complete conversion was obtained initially with all catalysts but it fell with time on stream as the catalysts deactivated. Table 2 presents the selectivity to ethylene and propylene and the ethylene/propylene product ratio at the point where conversion was 99% for each catalyst.

TABLE 2

Effect of Crystal Dimension on Ethylene/Propylene Production

| Catalyst I.D. | Average Smallest Dimension (Microns) | Crystal Morphology | $C_2^= + C_3^=$ Selectivity (%) | $C_2^=/C_3^=$ |
|---|---|---|---|---|
| A | 0.07 | Thin plates | 82.4 | 1.17 |
| B | 0.08 | Plates | 79.2 | 1.18 |
| C | 0.09 | Thin Plates | 82.2 | 1.25 |
| D | 0.13 | Plates | 80.8 | 1.40 |
| E | 0.17 | Plates | 81.2 | 1.41 |
| F | 0.58 | Cubic | 78.7 | 1.48 |

The average smallest crystallite dimension was determined by measuring 20 representative crystallites in one or more micrographs obtained using a Scanning Electron Microscope at 30,000× magnification. The data indicate that when the smallest crystal dimension is greater than 0.1 micron and the crystal morphology is plates, a greater amount of ethylene is produced. It is also observed that when the crystal morphology is cubic and the smallest dimension is greater than 0.2 microns, one obtains the highest production of ethylene. Note that when the smallest dimension is less than 0.1, one obtains poor results (greater propylene production) even though the crystal morphology is plates.

EXAMPLE 3

A second series of molecular sieves (SAPOs) with various amounts of silicon were prepared by the following procedure. In a container orthophosphoric acid (85%) was combined with water. To this there was added a silica sol and a 35 wt. % aqueous solution of tetraethylammonium hydroxide (TEAOH) or a mixture of di (n-propyl) diamine ($nPr_2NH$) and TEAOH. Finally, alumina in the form of pseudo-boehmite along with water and SAPO-34 seed material were added and blended in. The resulting mixtures had compositions in molar oxide ratios as set forth in Table 3 below.

TABLE 3

Reaction Mixture Compositions For SAPOs

| Sample I.D. | Reaction Time | TEAOH | $SiO_2$ | $Al_2O_3$ | $P_2O_5$ | $H_2O$ |
|---|---|---|---|---|---|---|
| G | 72 | 1.0 | 0.05 | 1.0 | 1.0 | 35 |
| H | 24 | 1.0 | 0.05 | 1.0 | 1.0 | 35 |
| I | 48 | 1.0 | 0.10 | 1.0 | 1.0 | 35 |
| J | 48 | 1.0 | 0.20 | 1.0 | 1.0 | 35 |
| K | 48 | 1.0 | 0.30 | 1.0 | 1.0 | 35 |
| $L^1$ | 72 | 1.0 | 0.40 | 1.0 | 1.0 | 35 |
| $M^2$ | 17 | * | 0.60 | 1.0 | 1.0 | 50 |

* 2.0 $n-Pr_2NH$ and 0.5 TEAOH
[1] no 100° C. hold
[2] no 100° C. hold, reaction temperature 175° C.

The mixture was now placed in a steel pressure reactor equipped with a turbine stirrer. The mixture was now stirred and heated to 100° C., held at 100° C. for 6 hours, then heated to 150° C. or 175° C. and held there for the reaction time. Finally, the reaction mixture was cooled to ambient temperature and the solid product recovered by centrifugation and washed with water. All the products were analyzed and found to be SAPO-34 molecular sieves.

EXAMPLE 4

The catalysts prepared in Example 3 were evaluated for the conversion of methanol to light olefins in a fixed bed pilot plant. A 4 gram sample in the form of 20–40 mesh agglomerates was used for the testing. Before testing, each sample was calcined in air in a muffle oven at 650° C. for 2 hours and then pre-treated in situ by heating to 400° C. for 1 hour under nitrogen. The pretreated sample was now contacted with a feed consisting of methanol and $H_2O$ in a 1/0.44 molar ratio at 400° C., 5 psig and 1 $hr^{-1}$ methanol WHSV. The composition of the effluent was measured by an on-line GC after 30 minutes on stream to determine initial conversion and selectivities. Complete conversion was obtained initially with all catalysts but it fell with time on stream as the catalysts deactivated. Table 4 presents the selectivity to ethylene and propylene and the ethylene/propylene product ratio at the point where conversion was 99% for each catalyst.

TABLE 4

Effect of Silicon Content on Olefin Production

| Catalyst I.D. | Si (%)* | $C_2^=+C_3^=$ Selectivity | $C_{4+}$ Selectivity (%) | $C_2^=/C_3^=$ | Coke wt. % |
|---|---|---|---|---|---|
| G | 1.6 | 81.3 | 15.8 | 1.13 | 15.2 |
| H | 1.7 | 80.9 | 15.9 | 1.12 | 16.0 |
| I | 3.2 | 82.5 | 12.9 | 1.30 | 19.0 |
| J | 5.2 | 83.7 | 12.1 | 1.36 | 21.6 |
| K | 6.7 | 84.8 | 9.6 | 1.23 | 19.4 |
| L | 9.5 | 78.8 | 16.9 | 0.96 | 20.4 |
| M | 14.0 | 73.0 | 22.1 | 0.82 | 13.4 |

*% of T atoms

The results in Table 4 show that selectivity to ethylene and propylene increase in the silicon range of about 2% to about 8% while production of $C_{4+}$ byproducts decreases within the same range. It is also observed that the $C_2^=+C_3^=$ selectivity increases more between 2% and 7% silicon and the most between 3% and 6.8% silicon.

What is claimed is:

1. A process for converting methanol to light olefins comprising contacting the methanol with a catalyst at conversion conditions to provide the olefins, the catalyst comprising a crystalline metallo aluminophosphate molecular sieve having a chemical composition on an anhydrous basis expressed by an empirical formula of:

$$(EL_xAl_yP_z)O_2$$

where EL is a metal selected from the group consisting of silicon, magnesium, zinc, iron, cobalt, nickel, manganese, chromium and mixtures thereof, "x" is the mole fraction of EL and has a value of about 0.02 to about 0.08, "y" is the mole fraction of Al and has a value of at least 0.01, "z" is the mole fraction of P and has a value of at least 0.01 and x+y+z=1, the molecular sieve characterized in that it has predominantly a plate crystal morphology, wherein the average smallest crystal dimension is at least 0.1 micron and has an aspect ratio of less than or equal to 5.

2. The process of claim 1 where the EL metal is selected from the group consisting of silicon, magnesium, cobalt and mixtures thereof.

3. The process of claim 2 where EL is silicon.

4. The process of claim 3 where the silicon aluminophosphate has the crystal structure of SAPO-34.

5. The process of claim 1 where "x" has a value of about 0.02 to about 0.07.

6. The process of claim 1 where "x" has a value of about 0.03 to about 0.068.

7. The process of claim 1 where the catalyst comprises a metallo-alumino-phosphate molecular sieve and an inorganic oxide binder.

8. The process of claim 7 where the binder is selected from the group consisting of alumina, silica, aluminum phosphate, silica-alumina and mixtures thereof.

9. The process of claim 7 where the molecular sieve is present in an amount from about 10 to about 90 weight percent of the catalyst.

10. The process of claim 7 where the molecular sieve is present in an amount from about 30 to about 70 weight percent of the catalyst.

11. The process of claim 1 where the conversion conditions are a temperature of about 300° C. to about 600° C., a pressure of about 0 kPa to about 17224 kPa (250 psig) and a weight hourly space velocity of about 1 to about 100 $hr^{-1}$.

12. The process of claim 1 where the average smallest crystal dimension is at least 0.2 microns.

13. The process of claim 1 where the aspect ratio is less than or equal to 2 and the crystal morphology is cubic.

14. A process for converting methanol to light olefins comprising contacting the methanol with a catalyst at conversion conditions to provide the olefins, the catalyst comprising a crystalline silico aluminophosphate molecular sieve having a chemical composition on an anhydrous basis expressed by an empirical formula of:

$$(Si_xAl_yP_z)O_2$$

where "x" is the mole fraction of Si and has a value of about 0.02 to about 0.08, "y" is the mole fraction of Al and has a value of at least 0.01, "z" is the mole fraction of P and has a value of at least 0.01 and x+y+z=1, the molecular sieve characterized in that it has predominantly a plate crystal morphology, wherein the average smallest crystal dimension is at least 0.1 micron and has an aspect ratio of less than or equal to 5 and the conversion conditions comprise a temperature of about 300° C. to about 600° C., a pressure of about 0 kPa to about 17224 kPa (250 psig) and a weight hourly space velocity of about 1 to about 100 $hr^{-1}$.

15. The process of claim 14 where the catalyst comprises silico-aluminophosphate molecular sieve and an inorganic oxide binder.

16. The process of claim 15 where the binder is selected from the group consisting of alumina, silica, aluminum phosphate, silica-alumina and mixtures thereof.

17. The process of claim 15 where the molecular sieve is present in an amount from about 10 to about 90 weight percent of the catalyst.

18. The process of claim 15 where the molecular sieve is present in an amount from 30 to about 70 weight percent of the catalyst.

19. The process of claim 14 where the average smallest crystal dimension is at least 0.2 microns.

20. The process of claim 14 where the aspect ratio is less than or equal to 2 and the crystal morphology is cubic.

21. The process of claim 14 where "x" has a value of about 0.02 to about 0.07.

22. The process of claim 14 where "x" has a value of about 0.03 to about 0.068.

23. The process of claim 14 where the silicon aluminophosphate has the crystal structure of SAPO-34.

* * * * *